(12) United States Patent
Mroczkowski et al.

(10) Patent No.: US 9,549,820 B2
(45) Date of Patent: Jan. 24, 2017

(54) GLENOID IMPLANT WITH SYNTHETIC LABRUM

(75) Inventors: Matthew L. Mroczkowski, Fort Wayne, IN (US); Russell M. Parrott, Warsaw, IN (US); Brian H. Thomas, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 1180 days.

(21) Appl. No.: 12/823,535

(22) Filed: Jun. 25, 2010

(65) Prior Publication Data

US 2010/0331990 A1 Dec. 30, 2010

Related U.S. Application Data

(60) Provisional application No. 61/220,316, filed on Jun. 25, 2009.

(51) Int. Cl.
| | | |
|---|---|---|
| *A61F 2/40* | (2006.01) | |
| *A61F 2/30* | (2006.01) | |
| *A61F 2/34* | (2006.01) | |
| *A61F 2/38* | (2006.01) | |

(52) U.S. Cl.
CPC .......... *A61F 2/4081* (2013.01); *A61F 2/30965* (2013.01); *A61F 2/34* (2013.01); *A61F 2/38* (2013.01); *A61F 2002/302* (2013.01); *A61F 2002/30004* (2013.01); *A61F 2002/30014* (2013.01); *A61F 2002/30016* (2013.01); *A61F 2002/3092* (2013.01); *A61F 2002/3093* (2013.01); *A61F 2002/30331* (2013.01); *A61F 2002/30448* (2013.01); *A61F 2002/30461* (2013.01); *A61F 2002/30604* (2013.01); *A61F 2002/30611* (2013.01); *A61F 2002/30612* (2013.01); *A61F 2002/30733* (2013.01); *A61F 2002/30934* (2013.01); *A61F 2220/005* (2013.01); *A61F 2220/0033* (2013.01); *A61F 2220/0075* (2013.01); *A61F 2230/0065* (2013.01); *A61F 2250/0014* (2013.01);
(Continued)

(58) Field of Classification Search
CPC ............ A61F 2/4081; A61F 2002/4022; A61F 2002/4025; A61F 2002/3429; A61F 2002/3435; A61F 2002/3437; A61F 2002/3443; A61F 2002/30611; A61F 2002/30612; A61F 2002/30014; A61F 2002/30016; A61F 2002/30021; A61F 2002/30563
See application file for complete search history.

(56) References Cited

U.S. PATENT DOCUMENTS 3,978,528 A * 9/1976 Crep .......................... 623/19.12
5,171,322 A    12/1992 Kenny
(Continued)

OTHER PUBLICATIONS

Jason Cary et al., "In situ compressive properties of the glenoid labrum," 2000 John Wiley & Sons, Inc., pp. 711-716.
(Continued)

*Primary Examiner* — Thomas J Sweet
*Assistant Examiner* — Cheryl Miller
(74) *Attorney, Agent, or Firm* — Schwegman Lundberg & Woessner, P.A.

(57) ABSTRACT

A prosthetic glenoid component for replicating the behavior of a patient's natural glenoid includes a rim that replicates the patient's natural glenoid labrum.

11 Claims, 4 Drawing Sheets

(52) U.S. Cl.
CPC ............... *A61F 2250/0018* (2013.01); *A61F 2310/00095* (2013.01); *A61F 2310/00131* (2013.01)

(56) References Cited

U.S. PATENT DOCUMENTS

| | | | |
|---|---|---|---|
| 5,534,028 A * | 7/1996 | Bao | A61F 2/441 606/247 |
| 5,711,960 A | 1/1998 | Shikinami | |
| 5,746,963 A | 5/1998 | Hogg | |
| 6,096,083 A * | 8/2000 | Keller | A61F 2/32 623/18.11 |
| 6,361,729 B1 | 3/2002 | Strover et al. | |
| 6,406,495 B1 | 6/2002 | Schoch | |
| 6,514,287 B2 | 2/2003 | Ondria et al. | |
| 6,629,997 B2 | 10/2003 | Mansmann | |
| 6,994,730 B2 | 2/2006 | Posner | |
| 7,291,169 B2 | 11/2007 | Hodorek | |
| 7,799,083 B2 * | 9/2010 | Smith et al. | 623/17.16 |
| 8,764,829 B2 * | 7/2014 | Marvel | A61F 2/30756 623/14.12 |
| 2003/0074077 A1 * | 4/2003 | Taylor | 623/22.26 |
| 2004/0051213 A1 * | 3/2004 | Muratoglu | A61F 2/30 264/494 |
| 2004/0133275 A1 | 7/2004 | Mansmann | |
| 2004/0133276 A1 | 7/2004 | Lang et al. | |
| 2004/0138754 A1 | 7/2004 | Lang et al. | |
| 2005/0221703 A1 | 10/2005 | Stone | |
| 2005/0222687 A1 | 10/2005 | Vunjak-Novakovic et al. | |
| 2006/0069443 A1 * | 3/2006 | Deffenbaugh | A61F 2/4081 623/19.11 |
| 2006/0085080 A1 | 4/2006 | Bechgaard et al. | |
| 2007/0038302 A1 | 2/2007 | Shultz et al. | |
| 2007/0050038 A1 * | 3/2007 | Snell | A61F 2/442 623/17.16 |
| 2007/0100450 A1 | 5/2007 | Hodorek | |
| 2007/0179607 A1 * | 8/2007 | Hodorek et al. | 623/14.12 |
| 2007/0219638 A1 * | 9/2007 | Jones et al. | 623/19.11 |
| 2007/0293947 A1 | 12/2007 | Mansmann | |
| 2008/0015707 A1 * | 1/2008 | Lambert et al. | 623/22.17 |
| 2008/0086210 A1 | 4/2008 | Fox | |
| 2008/0097606 A1 | 4/2008 | Cragg et al. | |
| 2008/0234820 A1 | 9/2008 | Felt et al. | |
| 2008/0306609 A1 * | 12/2008 | Lee | A61B 17/72 623/23.58 |
| 2009/0222098 A1 * | 9/2009 | Trieu | A61F 2/442 623/17.16 |

OTHER PUBLICATIONS

C.D. Smith et al., "Tensil properties of the human glenoid labrum,", 2007 the Authors, Journal compilation 2007 Anatomical Society of Breat Britain and Ireland, pp. 49-54.

DE Cooper et al., "Anatomy, histology, and vascularity of the glenoid labrum. An anatomical study," The Journal of Bone & Joint Surgery, vol. 74-A, No. 1, Jan. 1992, pp. 46-52.

\* cited by examiner

GLENOID IMPLANT WITH SYNTHETIC LABRUM

CROSS REFERENCE TO RELATED APPLICATION

This application claims priority from U.S. Provisional Patent Application Ser. No. 61/220,316, entitled "Glenoid Implant with Synthetic Labrum," filed Jun. 25, 2009, the disclosure of which is hereby expressly incorporated by reference herein in its entirety.

BACKGROUND

1. Field of the Invention

The present invention relates to orthopedic prostheses. More particularly, the present invention relates to prosthetic glenoid components of the type used in shoulder arthroplasty procedures.

2. Description of the Related Art

The shoulder or glenohumeral joint allows for articulation of a generally ball-shaped humeral head within a socket formed by the scapula, called the glenoid. In a natural, healthy shoulder joint, articular cartilage covers the articular portions of the glenoid and the humeral head to facilitate movement of the shoulder joint. The natural glenoid is small in surface area compared to the natural humeral head, which makes the shoulder joint vulnerable to instability.

Prosthetic shoulder components may be used to replace some or all of a patient's shoulder joint to restore or increase use of the shoulder joint following a traumatic injury or deterioration due to aging or illness, for example. The natural glenoid may be replaced with a prosthetic glenoid component, and the natural humeral head may be replaced with a prosthetic humeral component.

SUMMARY

A prosthetic glenoid component is provided to replicate the behavior of a natural, healthy glenoid. The prosthetic glenoid component includes a rim that replicates a natural glenoid labrum.

According to an embodiment of the present invention, a prosthetic socket is provided that is configured for securement to a patient's bone and for articulation with an adjacent head. The prosthetic socket includes a base configured for securement to the patient's bone, a bearing component coupled to the base, the bearing component formed of a first material and including an outer periphery, and a rim coupled to the base to substantially surround the outer periphery of the bearing component, the rim cooperating with the bearing component to define a socket that is dimensioned to receive the adjacent head, the rim formed of a second material that is more compliant than the first material of the bearing component.

According to another embodiment of the present invention, a prosthetic glenoid component is provided that is configured for securement to a scapula and for articulation with an adjacent humeral component, the scapula including a superior portion and an inferior portion. The prosthetic glenoid component includes a base having a bone-contacting surface configured rest against the scapula, and a bearing layer coupled to the base and having a concave articulating surface configured for articulation with the adjacent humeral component, the articulating surface including a central region and a peripheral region that surrounds the central region of the articulating surface and that is more compliant than the central region of the articulating surface.

According to yet another embodiment of the present invention, a method of repairing a patient's shoulder joint, the patient's shoulder joint including a scapula having a glenoid and a humerus having a head. The method includes the steps of: resecting the patient's scapula to remove the glenoid; providing a prosthetic glenoid component to replace the resected glenoid, the prosthetic glenoid component including a base having a bone-contacting surface and a bearing layer coupled to the base and including a concave articulating surface, the articulating surface including a central region and a peripheral region that surrounds the central region of the articulating surface and that is more compliant than the central region of the articulating surface; and positioning the bone-contacting surface of the base against the resected scapula.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 8:
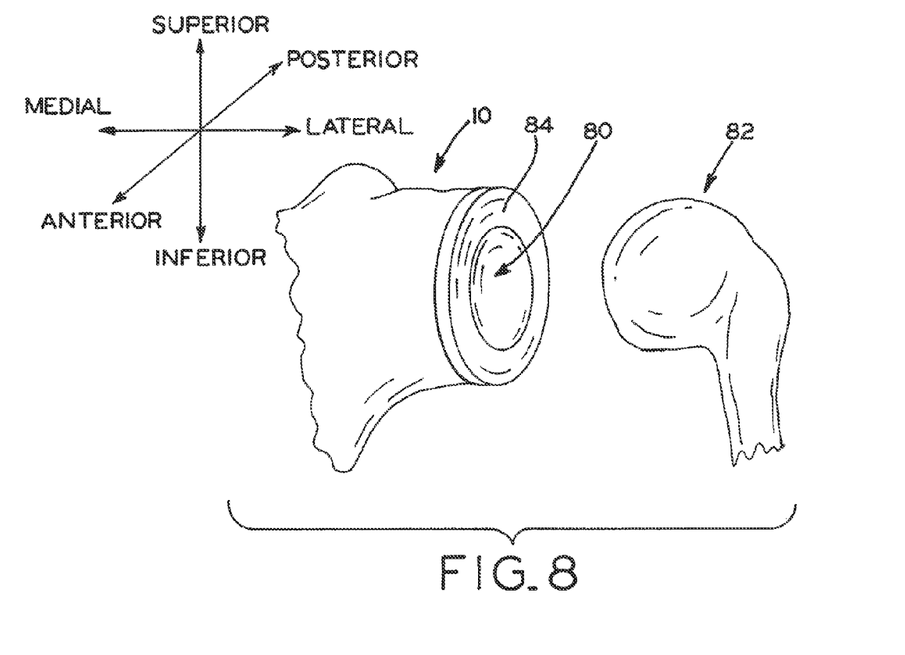
FIG. 8 is an exploded perspective view of a natural scapula and a natural humeral head of a patient's left shoulder joint.

A natural shoulder joint is depicted in FIG. 8 and includes a patient's scapula 10 and humeral head 82. Scapula 10 of the patient's shoulder joint forms a socket, known as the glenoid 80, that is shaped to articulate with humeral head 82. In a healthy shoulder joint, scapula 10 includes a cartilage rim, known as the glenoid labrum 84, that surrounds the outer periphery of glenoid 80. Glenoid labrum 84 may include a thick, dense layer of fibrocartilagenous tissue. During articulation with humeral head 82, glenoid labrum 84 stabilizes the patient's shoulder joint, especially at extreme positions of humeral head 82, while also permitting free movement of humeral head 82. Also, glenoid labrum 84 provides an attachment site for ligaments of the patient's shoulder joint.

Figure 1:
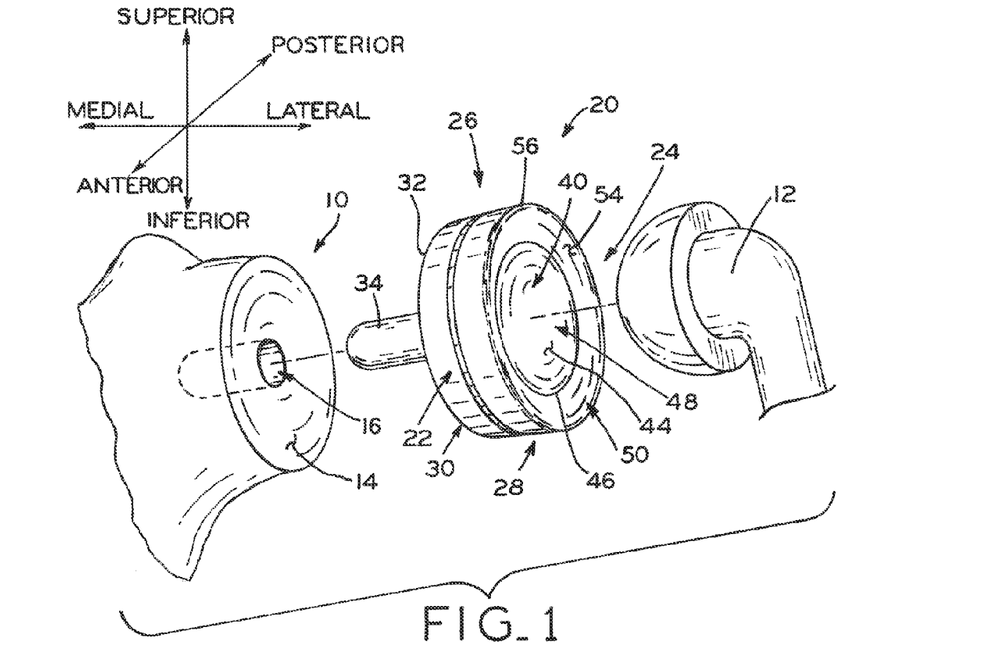
FIG. 1 is an exploded, perspective view of a prosthetic glenoid component and a prosthetic humeral component for replacing a patient's left shoulder joint.

A resected shoulder joint is depicted in FIG. 1. The illustrated scapula 10 has been resected or otherwise prepared for a shoulder arthroplasty procedure. Specifically, glenoid 80 and glenoid labrum 84 (FIG. 8) of scapula 10 have been resected in preparation for the shoulder arthroplasty procedure. The present invention may also be applicable to hip arthroplasty procedures and knee arthroplasty procedures, for example.

An exemplary prosthetic glenoid component 20 is provided to replicate the behavior of the resected glenoid 80 and glenoid labrum 84 (FIG. 8). As shown in FIG. 1, prosthetic glenoid component 20 includes anterior portion 22, posterior portion 24, superior portion 26, and inferior portion 28. Prosthetic glenoid component 20 further includes base 30, bearing component 40, and rim 50.

Figure 2:
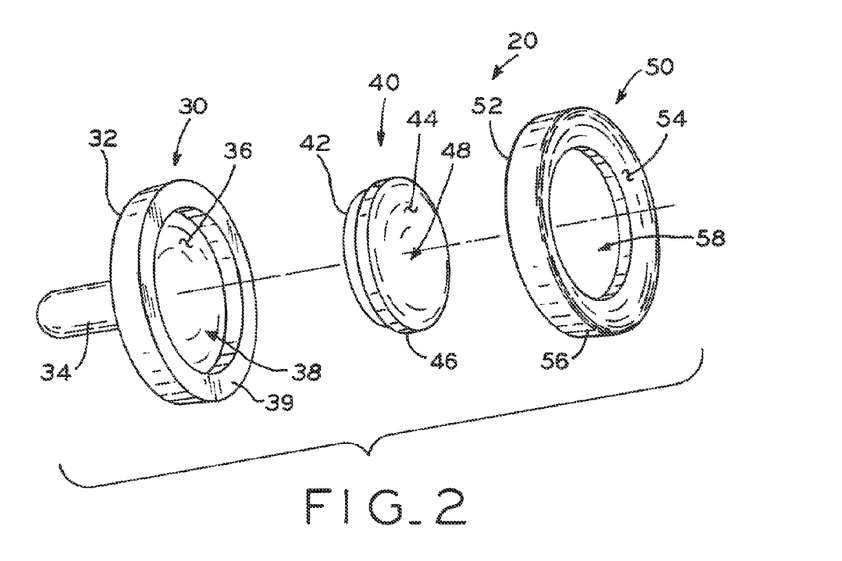
FIG. 2 is an exploded perspective view of the prosthetic glenoid component of FIG. 1, the prosthetic glenoid component including a base, a bearing component, and a rim.

Referring to FIGS. 1 and 2, base 30 of prosthetic glenoid component 20 includes bone-contacting surface 32 and a projection, such as stem 34, that extends from bone-contacting surface 32. The projection may also include a peg, a keel, a bone screw, or combinations thereof. With bone-contacting surface 32 of base 30 resting against resected surface 14 of scapula 10, stem 34 of base 30 extends medially into drilled bore 16 in scapula 10 to anchor prosthetic glenoid component 20 to scapula 10. For example, bore 16 in scapula 10 may receive bone cement to anchor stem 34 of prosthetic glenoid component 20 to scapula 10. Base 30 of prosthetic glenoid component 20 also includes mating surface 36 located opposite of bone-contacting surface 32, as shown in FIG. 2.

Base 30 of prosthetic glenoid component 20 may be constructed of a biocompatible ceramic or metal, including, but not limited to, titanium, a titanium alloy, cobalt chromium, or cobalt chromium molybdenum. Also, base 30 of prosthetic glenoid component 20 may be constructed completely or partially of a porous material that promotes bone ingrowth into bone-contacting surface 32 of base 30 and/or stem 34 of base 30. For example, base 30 may be constructed of porous tantalum or a highly porous biomaterial. A highly porous biomaterial is useful as a bone substitute and as cell and tissue receptive material.

A highly porous biomaterial may have a porosity as low as 55, 65, or 75 percent and as high as 80, 85, or 90 percent. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861, the disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of prosthetic glenoid component 20 to scapula 10.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

As shown in FIGS. 1 and 2, base 30 of prosthetic glenoid component 20 defines socket 38. More particularly, mating surface 36 of base 30 defines socket 38. Socket 38 is sized to receive bearing component 40 of prosthetic glenoid component 20, as described further below. For example, bearing component 40 may be a modular component that is selected intraoperatively and secured to base 30, or bearing component 40 may be integrally connected to base 30. As shown in FIG. 2, mating surface 36 of base 30 includes lip 39 that surrounds socket 38 to support bearing component 40.

Referring still to FIGS. 1 and 2, bearing component 40 of prosthetic glenoid component 20 includes mating surface 42, articulating surface 44 located opposite of mating surface 42, and outer periphery 46. Also, bearing component 40 of prosthetic glenoid component 20 defines socket 48. More particularly, articulating surface 44 of bearing component 40 defines socket 48. An adjacent natural humeral head 82 (FIG. 8) or prosthetic humeral component 12 (FIG. 1) may be received within socket 48 to articulate with articulating surface 44 of bearing component 40.

To facilitate smooth articulation with an adjacent natural humeral head 82 (FIG. 8) or prosthetic humeral component 12 (FIG. 1), bearing component 40 of prosthetic glenoid component 20 may be constructed of a smooth, durable material, such as a polymer. For example, bearing component 40 of prosthetic glenoid component 20 may be constructed of a hydrogel, poly ether ether ketone (PEEK), fiber reinforced poly ether ether ketone, ultrahigh molecular weight polyethylene (UHMWPE), crosslinked ultrahigh molecular weight polyethylene, polyurethane, or polyether ketone ether ether ketone.

Figure 3:
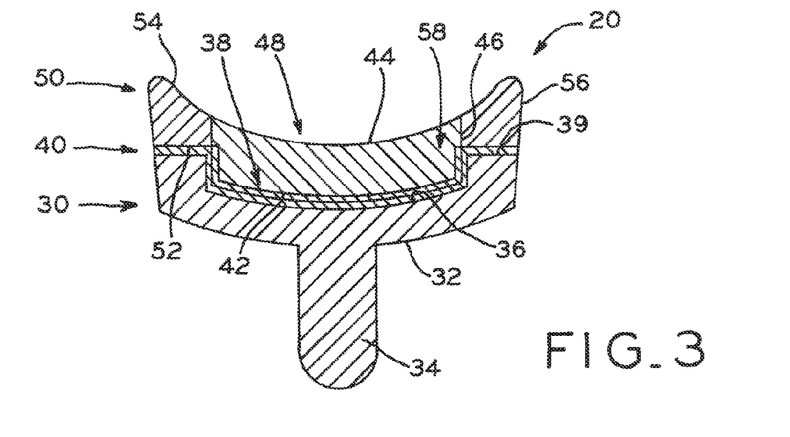
FIG. 3 is a cross-sectional view of the prosthetic glenoid component of FIG. 2, wherein the rim is molded onto the base of the prosthetic glenoid component.
Figure 4:
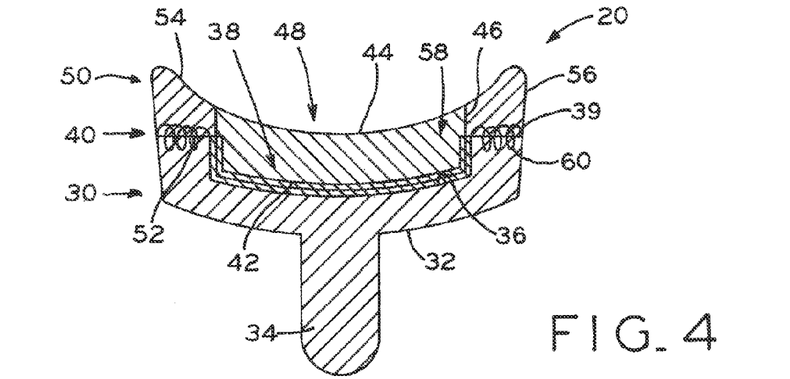
FIG. 4 is a cross-sectional view similar to FIG. 3, wherein the rim is sutured onto the base of the prosthetic glenoid component.
Figure 5:
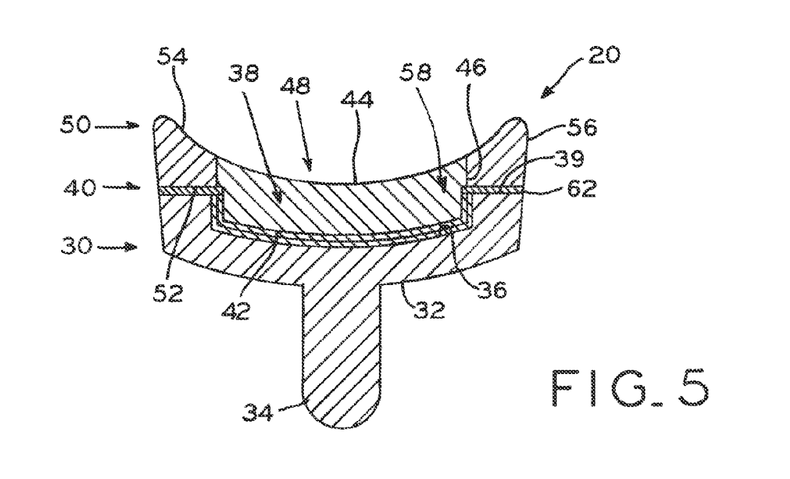
FIG. 5 is a cross-sectional view similar to FIG. 3, wherein the rim is adhered onto the base of the prosthetic glenoid component.
Figure 6:
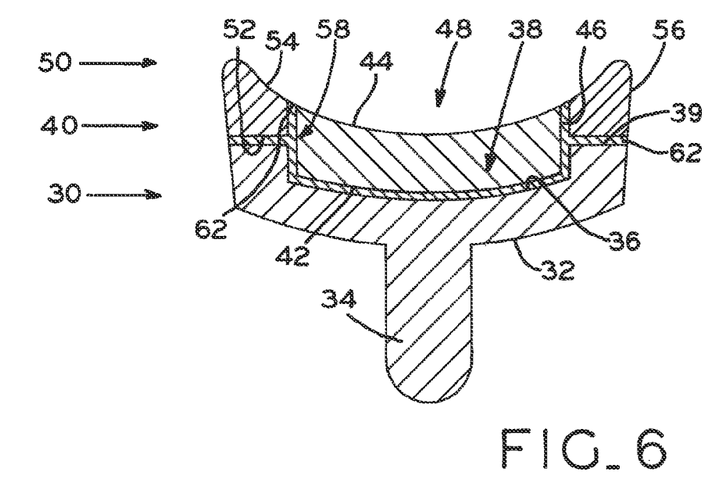
FIG. 6 is a cross-sectional view similar to FIG. 3, wherein the rim is adhered to the bearing component of the prosthetic glenoid component.

As discussed above, socket 38 of base 30 is sized to receive bearing component 40. Base 30 and bearing component 40 of prosthetic glenoid component 20 may form an assembly by attaching, adhering, or otherwise securing mating surface 42 of bearing component 40 to mating surface 36 of base 30. According to an exemplary embodiment of the present invention, a polymeric bearing component 40 may be molded onto and interdigitate into a porous base 30 to form a secure, unitary assembly, as shown in FIGS. 3-5. According to another exemplary embodiment of the present invention, bearing component 40 is a modular component that may be selected intraoperatively and adhered to base 30, such as with adhesive 62, as shown in FIG. 6.

Referring again to FIGS. 1 and 2, rim 50 of prosthetic glenoid component 20 includes mating surface 52, articulating surface 54 located opposite of mating surface 52, and outer periphery 56. Also, rim 50 of prosthetic glenoid component 20 defines bore 58. Bore 58 of rim 50 is sized to receive bearing component 40, such that rim 50 substantially surrounds outer periphery 46 of bearing component 40, as shown in FIG. 1.

Articulating surface 54 of rim 50 is configured to cooperate with articulating surface 44 of bearing component 40 to receive and articulate with an adjacent natural humeral head 82 (FIG. 8) or prosthetic humeral component 12 (FIG. 1). According to an exemplary embodiment of the present invention, articulating surfaces 44, 54, cooperate to define a smooth, substantially continuous surface to receive and articulate with the adjacent natural humeral head 82 (FIG. 8) or prosthetic humeral component 12 (FIG. 1). As shown in FIGS. 3-5, articulating surface 54 of rim 50 extends radially outwardly beyond outer periphery 46 of bearing component 40 and above articulating surface 44 of bearing component 40.

Referring to FIGS. 3-5, articulating surface 54 of rim 50 may have a concave radius of curvature. The curvature of rim 50 may be greater than, less than, or substantially equal to the curvature of articulating surface 44 of bearing component 40 that defines socket 48. For example, as shown in FIG. 3, articulating surface 44 of bearing component 40 and articulating surface 54 of rim 50 have a substantially constant radius of curvature.

The radius of curvature of the patient's natural glenoid labrum 84 (FIG. 8) may vary depending on anatomical location. Therefore, to replicate the patient's natural glenoid labrum 84, the curvature of rim 50 may vary across the periphery of prosthetic glenoid component 20. Also, at any particular radial location, it is within the scope of the present invention that bearing component 40 and/or rim 50 may have more than one radius of curvature. For example, the curvature of bearing component 40 may be shallow near the center of bearing component 40 and may be steep near outer periphery 46 of bearing component 40.

Referring still to FIGS. 3-5, rim 50 may have a substantially wedge-shaped cross-section, such that rim 50 increases in thickness from bore 58 to outer periphery 56. In this embodiment, the distance between mating surface 52 and articulating surface 54 of rim 50 may increase from bore 58 to outer periphery 56.

The size and shape of the patient's natural glenoid labrum 84 (FIG. 8) may vary depending on anatomical location. Therefore, to replicate the patient's natural glenoid labrum 84, the thickness and/or width of rim 50 may vary across the periphery of prosthetic glenoid component 20.

Rim 50 of prosthetic glenoid component 20 may have different mechanical, physical, and/or chemical properties than bearing component 40 so that the material of rim 50 is more compliant and/or flexible than the material of bearing component 40. In some embodiments, rim 50 and bearing component 40 may be constructed of different materials. For example, bearing component 40 of prosthetic glenoid component 20 may be constructed of UHMWPE, and rim 50 of prosthetic glenoid component 20 may be constructed of a more compliant hydrogel material, silicone material, woven material, or elastomer. In other embodiments, rim 50 and bearing component 40 may be constructed of the same material (e.g. having the same chemical make-up) that has been processed to vary the flexibility of the material.

According to an exemplary embodiment, the material used to construct rim 50 may have a lower molecular weight than the material used to construct bearing component 40. For example, both rim 50 and bearing component 40 may be constructed of a polyvinyl alcohol based hydrogel, the material of rim 50 having a lower molecular weight (e.g., 186,000 daltons) than the material of bearing component 40 (e.g., 250,000 daltons). The change in molecular weight may be produced by separate solution cast steps, injection molding, or centrifugal molding, for example.

According to another exemplary embodiment, the material used to construct rim 50 may have a lower polymer concentration/higher water concentration than the material used to construct bearing component 40. For example, both rim 50 and bearing component 40 may be constructed of a polyvinyl alcohol based hydrogel, the material of rim 50 having a lower polymer concentration/higher water concentration (e.g., 40 weight % polymer/60 weight % water) than the material of bearing component 40 (e.g., 70 weight % polymer/30 weight % water).

According to yet another exemplary embodiment, the material used to construct rim 50 may have a higher ratio of soft segments to hard segments than the material used to construct bearing component 40. For example, both rim 50 and bearing component 40 may be constructed of a material having hard to soft segments, such as polyurethane, which may be chemically processed to provide rim 50 having a higher ratio of soft segments to hard segments than bearing component 40. Two or more urethanes thermosets may be cast to produce a seamless device.

According to yet another exemplary embodiment, the material used to construct rim 50 may have a lower weave density than the material used to construct bearing component 40. It is within the scope of the present disclosure that rim 50 and bearing component 40 may be produced in a single mold using a layup method in which fibers, wovens, or non-wovens are strategically placed and then overmolded to produce the desired mechanical properties. The mechanical properties of rim 50 and bearing component 40 may also be customized by varying porosities and by using molecular weight blends, fillers, and/or plasticizers.

The compliancy of rim 50 may be determined based on various mechanical properties. In an exemplary embodiment, rim 50 may be constructed of a material that has a lower elastic modulus than the material of bearing component 40. For example, if bearing component 40 of prosthetic glenoid component 20 is constructed of UHMWPE having an elastic modulus under tension of approximately 900 MPa, rim 50 of prosthetic glenoid component 20 may be constructed of a more compliant polyvinyl alcohol (PVA) hydrogel having an elastic modulus under tension of less than approximately 2 MPa. In another exemplary embodiment, rim 50 may be constructed of a material that has a lower hardness than the material of bearing component 40. For example, if bearing component 40 of prosthetic glenoid component 20 is constructed of a D-scale polymer (e.g., 55D polyurethane), rim 50 of prosthetic glenoid component 20 may be constructed of a softer, A-scale polymer (e.g., 40A, 60A, or 80A polyurethane). Hardness may be measured using a variety of tests, such as the Rockwell hardness test or the Shore (Durometer) hardness test.

According to an exemplary embodiment of the present invention, rim 50 of prosthetic glenoid component 20 may be constructed of a material having mechanical properties similar to those of a natural glenoid labrum 84 (FIG. 8). Reported mechanical properties of a typical glenoid labrum 84 are provided in Table 1 below.

TABLE 1

| Mechanical Property | Location | Reported Value |
| --- | --- | --- |
| Elastic modulus (compression) | Inferior-anterior | 0.18 ± 0.17 MPa [1] |
| Elastic modulus (compression) | Inferior | 0.11 ± 0.16 MPa [1] |
| Elastic modulus (compression) | Inferior-posterior | 0.23 ± 0.20 MPa [1] |
| Elastic modulus (compression) | Superior-anterior | 0.19 ± 0.09 MPa [1] |

TABLE 1-continued

| Mechanical Property | Location | Reported Value |
| --- | --- | --- |
| Elastic modulus (compression) | Superior | 0.32 ± 0.22 MPa [1] |
| Elastic modulus (compression) | Superior-posterior | 0.41 ± 0.32 MPa [1] |
| Elastic modulus (tension) | Average of 8 radial sections | 22.8 ± 11.4 MPa [2] |
| Yield stress (tension) | Average of 8 radial sections | 2.5 ± 2.1 MPa [2] |

[1] Carey, Jason, et al., "In Situ Compressive Properties of the Glenoid Labrum," Journal of Biomedical Materials Research 51 (2000): 711-716.
[2] Smith, C.D., et al., "Tensile Properties of the Human Glenoid Labrum," Journal of Anatomy 212 (2008): 49-54.

According to yet another exemplary embodiment of the present invention, the mechanical properties of rim 50 may vary across the periphery of prosthetic glenoid component 20. As shown in Table 1 above, the mechanical properties of the typical glenoid labrum 84 (FIG. 8) may vary depending on anatomical location, most notably between the inferior and superior portions of glenoid labrum 84. Therefore, to replicate the patient's natural glenoid labrum 84, rim 50 may have a higher elastic modulus in superior portion 26 of prosthetic glenoid component 20 than in inferior portion 28 of prosthetic glenoid component 20 (FIG. 1). To accomplish these varied mechanical properties, rim 50 may be constructed of more than one material, or a single material may be treated to alter its mechanical properties, for example.

As mentioned above, and as illustrated in FIGS. 3-5, prosthetic glenoid component 20 may be formed with rim 50 substantially surrounding outer periphery 46 of bearing component 40. Rim 50 may be coupled to base 30 and/or bearing component 40 of prosthetic glenoid component 20. For example, rim 50 may be coupled to lip 39 of base 30 and/or outer periphery 46 of bearing component 40. Securing rim 50 to outer periphery 46 of bearing component 40, in particular, may provide an uninterrupted articular surface between rim 50 and bearing component 40.

Various methods may be used to couple rim 50 to base 30 and/or bearing component 40 of prosthetic glenoid component 20. Certain exemplary methods are described below with reference to FIGS. 3-7.

As shown in FIG. 3, a polymeric rim 50 may be molded onto and interdigitate into a porous base 30 to form a secure, unitary assembly. Like rim 50, bearing component 40 may also be molded onto and interdigitate into the porous base 30.

As shown in FIG. 4, rim 50 may be mechanically fastened to base 30 and/or bearing component 40, such as using sutures 60 to sew rim 50 onto base 30. It is also within the scope of the present invention that rim 50 may be nailed, stapled, tacked, or otherwise mechanically fastened to base 30 and/or bearing component 40.

As shown in FIG. 5, rim 50 may be adhered to base 30, such as with adhesive 62. Rim 50 may also be adhered to outer periphery 46 of bearing component 40 with adhesive 62, as shown in FIG. 6, to provide an uninterrupted articular surface 44, 54, between rim 50 and bearing component 40. It is also within the scope of the present invention that rim 50 may be chemically bonded to base 30 and/or bearing component 40.

Figure 7:
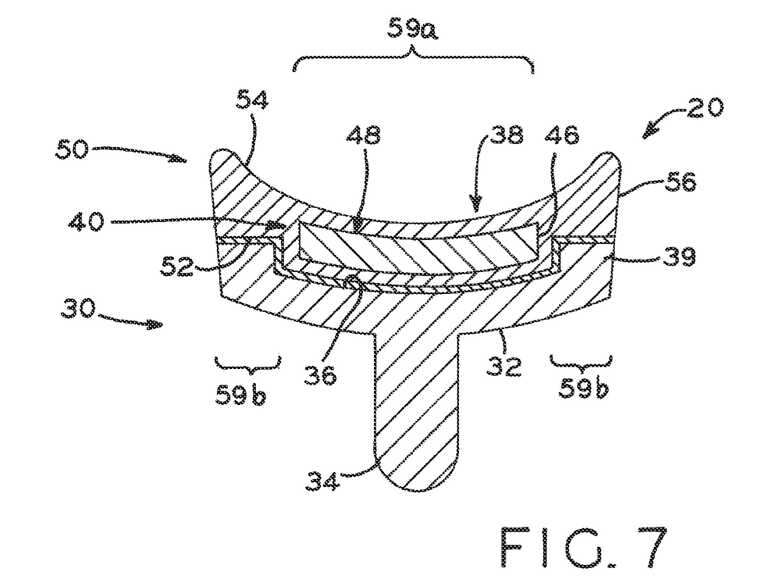
FIG. 7 is a cross-sectional view similar to FIG. 3, wherein the rim encases the bearing component of the prosthetic glenoid component.

As shown in FIG. 7, rim 50 may be overmolded onto bearing component 40, such that a thin layer of rim 50 encases bearing component 40. In this embodiment, articulating surface 54 of rim 50 may span across substantially the entire prosthetic glenoid component 20, with bearing component 40 lying beneath articulating surface 54 of rim 50.

Within central region 59a of rim 50, the presence of bearing component 40 may provide strength and rigidity to rim 50. Within peripheral region 59b of rim 50, the absence of bearing component 40 may allow rim 50 to retain some flexibility and resiliency.

According to an exemplary embodiment of the present invention, rim 50 may be a modular component. Rim 50 may be provided in various shapes, sizes, and materials and may be selected intraoperatively depending on the needs of each particular patient. After the desired rim 50 is selected, rim 50 may be attached intraoperatively to base 30 and/or bearing component 40, such as with sutures 60 (FIG. 4) or adhesive 62 (FIG. 5), for example.

According to another exemplary embodiment of the present invention, rim 50 may be attached to base 30 and/or bearing component 40 at selective locations to mimic a natural glenoid labrum 84 (FIG. 8), which has been shown to attach firmly at the inferior edge of glenoid 80 and loosely at the superior edge of glenoid 80. Therefore, rim 50 may be attached firmly at inferior portion 28 of prosthetic glenoid component 20 and loosely at superior portion 26 of prosthetic glenoid component 20 (FIG. 1).

According to yet another exemplary embodiment of the present invention, rim 50 may be treated for improved lubrication. Also, rim 50 may be configured to deliver biologically active agents, such as drugs, to the patient.

When implanted, rim 50 of prosthetic glenoid component 20 may replicate the behavior of a natural, healthy glenoid labrum 84 (FIG. 8). For example, like glenoid labrum 84, rim 50 of prosthetic glenoid component 20 may stabilize the shoulder joint by reducing edge loading on bearing component 40. Also, rim 50 of prosthetic glenoid component 20 may provide an attachment site for ligaments of the shoulder joint.

As mentioned above, the present invention may also be applicable to hip arthroplasty procedures and knee arthroplasty procedures. For example, a prosthetic tibial component may be provided with a rim to replicate the meniscus of a natural knee joint, and a prosthetic acetabular component may be provided with a rim to replicate the acetabular labrum.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A prosthetic socket configured for securement to a patient's bone and for articulation with an adjacent head, the prosthetic socket comprising:
   a base configured for securement to the patient's bone, the base having a bone-contacting surface and a projection that extends from the bone-contacting surface;
   a bearing component coupled to and contacting the base, the bearing component formed of a first material and including an outer periphery and a first articulation surface; and
   a rim coupled to the base such that the rim substantially surrounds the outer periphery of the bearing component, the rim including a second articulation surface, wherein the first articulation surface of the bearing component and the second articulation surface of the rim define a continuous articulation surface that is dimensioned to receive and articulate with the adjacent head, wherein the first articulation surface and the second articulation surface are each configured to articulate with the adjacent head, and wherein the rim is formed of a second material different from the first material, the second material being more compliant than the first material of the bearing component.

2. The prosthetic socket of claim 1, wherein the projection is configured to extend from the bone-contacting surface and into the patient's bone to anchor the prosthetic socket to the patient's bone.

3. The prosthetic socket of claim 1, wherein the rim is a ring-shaped component defining a central opening, wherein the bearing component is located in the central opening.

4. The prosthetic socket of claim 1, wherein the rim is at least one of molded, fastened, and adhered onto the base.

5. The prosthetic socket of claim 1, wherein the base is constructed of a porous material, the rim interdigitating into the porous material of the base.

6. The prosthetic socket of claim 1, wherein the first material of the bearing component includes at least one of poly ether ether ketone, fiber reinforced poly ether ether ketone, ultrahigh molecular weight polyethylene, crosslinked ultrahigh molecular weight polyethylene, polyurethane, and polyether ketone ether ether ketone, and the second material of the rim includes at one of hydrogel, silicone, a woven material, and an elastomer.

7. A prosthetic glenoid component configured for securement to a scapula and for articulation with an adjacent humeral component, the scapula including a superior portion and an inferior portion, the prosthetic glenoid component comprising:
a base comprising a bone-contacting surface configured to abut the scapula and a projection that extends from the bone-contacting surface configured to extend into the scapula; and
a bearing layer coupled to the base and comprising a concave articulating surface configured for articulation with the adjacent humeral component, the concave articulating surface including a central region formed of first material and a peripheral region formed of a second material different from the first material, the peripheral region surrounding the central region of the concave articulating surface, wherein the central region and the peripheral region of the concave articulating surface are configured to articulate with the adjacent humeral component, wherein the second material is more compliant than the first material, wherein the central region is a bearing component and the peripheral region is an outer rim that surrounds an outer periphery of the bearing component.

8. The prosthetic glenoid component of claim 7, wherein the peripheral region of the bearing layer includes a superior side that is configured to border the superior portion of the scapula and an inferior side that is configured to border the inferior portion of the scapula, the superior side of the peripheral region of the bearing layer being less compliant than the inferior side of the peripheral region of the bearing layer.

9. The prosthetic glenoid component of claim 7, wherein the outer rim is a ring-shaped component.

10. The prosthetic glenoid component of claim 7, wherein the first material of the bearing component includes at least one of poly ether ether ketone, fiber reinforced poly ether ether ketone, ultrahigh molecular weight polyethylene, crosslinked ultrahigh molecular weight polyethylene, polyurethane, and polyether ketone ether ether ketone, and the second material of the rim includes at one of hydrogel, silicone, a woven material, and an elastomer.

11. A prosthetic glenoid component configured for securement to a scapula and for articulation with an adjacent humeral component, the scapula including a superior portion and an inferior portion, the prosthetic glenoid component comprising:
a base comprising a bone-contacting surface configured to abut the scapula and a projection that extends from the bone-contacting surface configured to extend into the scapula; and
a bearing layer coupled to the base and comprising a concave articulating surface configured for articulation with the adjacent humeral component, the concave articulating surface including a central region formed of first material and a peripheral region formed of a second material different from the first material, the peripheral region surrounding the central region of the concave articulating surface, wherein the central region and the peripheral region of the concave articulating surface are configured to articulate with the adjacent humeral component, wherein the second material is more compliant than the first material, wherein the central region is a bearing component and the peripheral region is an outer rim that surrounds an outer periphery of the bearing component; wherein the bearing layer includes a superior side that is configured to border the superior portion of the scapula and an inferior side that is configured to border the inferior portion of the scapula, the inferior side of the bearing layer being more firmly coupled to the base than the superior side of the bearing layer.

* * * * *